(12) United States Patent
De Faveri et al.

(10) Patent No.: US 8,580,963 B2
(45) Date of Patent: Nov. 12, 2013

(54) METHOD FOR THE MANUFACTURING OF NALTREXONE

(75) Inventors: Carla De Faveri, Farra di Soligo (IT); Florian Anton Martin Huber, Dolo (IT); Mariano Stivanello, Schio (IT)

(73) Assignee: H. Lundbeck A/S, Valby (DK)

( * ) Notice: Subject to any disclaimer, the term of this patent is extended or adjusted under 35 U.S.C. 154(b) by 265 days.

(21) Appl. No.: 13/287,391

(22) Filed: Nov. 2, 2011

(65) Prior Publication Data

US 2012/0116085 A1    May 10, 2012

Related U.S. Application Data

(60) Provisional application No. 61/410,405, filed on Nov. 5, 2010, provisional application No. 61/489,701, filed on May 25, 2011.

(51) Int. Cl.
*C07D 489/08*    (2006.01)
*C07D 489/02*    (2006.01)

(52) U.S. Cl.
USPC ............................................. 546/45; 546/44

(58) Field of Classification Search
USPC ...................................................... 546/45, 44
See application file for complete search history.

(56) References Cited

U.S. PATENT DOCUMENTS 8,080,661 B2 * 12/2011 Wang et al. ..................... 546/74

FOREIGN PATENT DOCUMENTS

| WO | 91/05768 | 5/1991 |
|---|---|---|
| WO | 2008034973 | 3/2008 |
| WO | 2008138605 | 11/2008 |
| WO | 2010039209 | 4/2010 |

OTHER PUBLICATIONS

International Search Report and Written Opinion dated Dec. 21, 2011 issued in International Application No. PCT/DK2011/000128.

* cited by examiner

*Primary Examiner* — Charanjit Aulakh
(74) *Attorney, Agent, or Firm* — Mary Catherine Di Nunzio; Stephen G. Kalinchak

(57) ABSTRACT

The present invention relates to an improved process for producing naltrexone[17-(cyclopropylmethyl)-4,5α-epoxy-3,14-dihydroxy-morphinan-6-one] from noroxymorphone [4,5-α-epoxy-3,14-dihydroxy-morphinan-6-one] by alkylation with a cyclopropylmethyl halide.

13 Claims, No Drawings

METHOD FOR THE MANUFACTURING OF NALTREXONE

CROSS-REFERENCE TO RELATED APPLICATIONS

The present application claims the benefit of priority under 35 U.S.C. §119(e) of U.S. Provisional Patent Application No. 61/410,405, filed Nov. 5, 2010 and U.S. Provisional Patent Application No. 61/489,701, filed May 25, 2011, which are hereby incorporated by reference in their entirety.

FIELD OF THE INVENTION

The present invention relates to an improved process for producing naltrexone[17-(cyclopropylmethyl)-4,5α-epoxy-3,14-dihydroxy-morphinan-6-one] from noroxymorphone [4,5-α-epoxy-3,14-dihydroxy-morphinan-6-one] by alkylation with a cyclopropylmethyl halide.

BACKGROUND OF THE INVENTION

Nalmefene is a known opioid receptor antagonist which can inhibit pharmacological effects of both administered opioid agonists and endogenous agonists derived from the opioid system. The clinical usefulness of nalmefene as antagonist comes from its ability to promptly (and selectively) reverse the effects of these opioid agonists, including the frequently observed depressions in the central nervous system and the respiratory system.

Nalmefene has primarily been developed as the hydrochloride salt for use in the management of alcohol dependency, where it has shown good effect in doses of 10 to 40 mg taken when the patient experiences a craving for alcohol (Karhuvaara et al., *Alcohol. Clin. Exp. Res.*, (2007), Vol. 31 No. 7. pp 1179-1187). Additionally, nalmefene has also been investigated for the treatment of other addictions such as pathological gambling and addiction to shopping. In testing the drug in these developmental programs, nalmefene has been used, for example, in the form of a parenteral solution (Revex™).

Nalmefene is an opiate derivative quite similar in structure to the opiate antagonist naltrexone. Advantages of nalmefene compared to naltrexone include longer half-life, greater oral bioavailability and no observed liver toxicity.

Nalmefene can be produced from naltrexone by the Wittig reaction. Methods for preparation of nalmefene from naltrexone by the Wittig reaction has been described by Hanh et al., (*J. Med. Chem.*, 18, 259-262 (1975), Mallinckrodt (U.S. Pat. No. 4,751,307), Meltzner et al., (U.S. Pat. No. 4,535,157) and by H. Lundbeck (WO 2010/136039). By using the above-mentioned methods, the free base of nalmefene is obtained, which subsequently can be converted into the hydrochloride salt by use of conventional methods.

Naltrexone can be produced from noroxymorphone by various direct and indirect alkylation methods. One method is by direct alkylation of noroxymorphone with cyclopropylmethylbromide. This process has been disclosed in general terms by Rice in WO 91/05768. Sanofi-Avensis (WO 2008/034973) describes a process for obtaining naltrexone in 88.6% yield by reacting noroxymorphone hydrochloride with cyclopropylmethylbromide in dimethylacetamide in the presence of sodium hydrogen carbonate. Cilag (WO 2008/138605) describes N-alkylation of noroxymorphone with cyclopropylmethylbromide in N-methyl-pyrrolidone in the presence of sodium hydrogen carbonate. Mallinckrodt (WO 2010/039209) describes N-alkylation of noroxymorphone with cyclopropylmethylbromide in the presence of a protic solvent. Specific examples in WO 2010/039209 describe the addition of water, isopropanol or ethanol as the protic solvent.

There is a need within the field to improve the method of producing highly pure naltrexone and/or to find alternative processes for producing naltrexone. In particular, there is a need for a method that is readily applicable on industrial scale.

SUMMARY OF THE INVENTION

The present invention relates to an improved process for producing naltrexone[17-(cyclopropylmethyl)-4,5α-epoxy-3,14-dihydroxy-morphinan-6-one] from noroxymorphone [4,5-α-epoxy-3,14-dihydroxy-morphinan-6-one] by alkylation of noroxymorphone with a cyclopropylmethyl halide in N-ethyl-2-pyrrolidone as depicted in scheme 1 below.

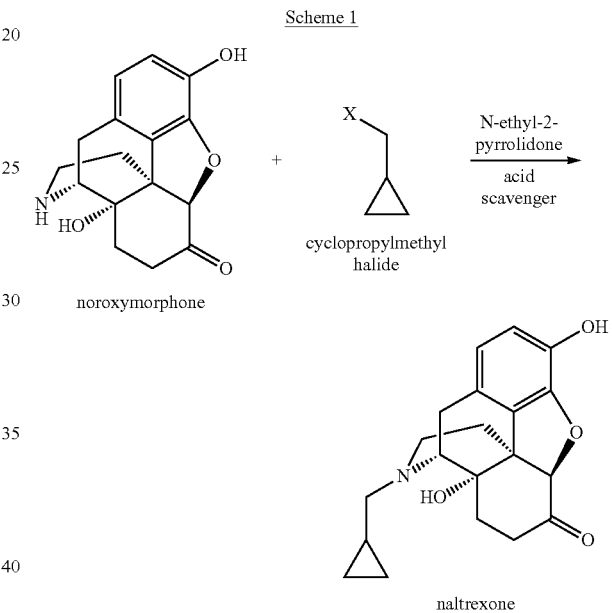

X is chosen from Br, Cl and I

In one embodiment, naltrexone obtained from the process of the invention is further processed e.g. by the Wittig reaction to nalmefene.

In one embodiment, the invention relates to a process for the manufacturing of nalmefene comprising the steps, i) manufacturing of naltrexone by a process of the invention, ii) further processing of naltrexone obtained from i) to nalmefene optionally by the Wittig reaction.

In one embodiment, the invention relates to naltrexone directly obtained by a process of the invention.

In one embodiment, the invention relates to nalmefene obtained from naltrexone, wherein said naltrexone is directly obtained by the process of the invention.

In one embodiment, the invention relates to a pharmaceutical composition comprising nalmefene obtained from naltrexone, wherein said naltrexone is directly obtained by the process of the invention.

Definitions

Throughout the description, the terms "naltrexone" and "nalmefene" are intended to include any forms of the compounds, such as the free base and pharmaceutically acceptable salts. The free base and pharmaceutically acceptable salts include anhydrous forms and solvated forms such as hydrates. The anhydrous forms and the solvates include amorphous and crystalline forms. In a particular embodiment naltrexone is in the form of the free base. In a particular embodiment nalmefene is in the form of the hydrochloride.

In the present context, examples of "cyclopropylmethyl halides" include cyclopropylmethyl bromide, cyclopropylmethyl chloride, cyclopropylmethyl iodide. In a particular embodiment, the term "cyclopropylmethyl halide" refers to cyclopropylmethyl bromide.

In the present context, a "non-protic solvent" refers to any non-protic solvent. Non-limiting examples of non-protic solvents include hydrocarbons, ketones, esters and ethers. In a particular embodiment, the term "non-protic solvent" refers to toluene.

In the present context, an "acid scavenger" refers to a compound selected from organic and inorganic bases, and combinations hereof. Examples include borate salts, phosphate salts, bicarbonate salts (such as $KHCO_3$, $NaHCO_3$, $LiHCO_3$ and the like), carbonate salts (such as $K_2CO_3$, $Na_2CO_3$, $Li_2CO_3$ and the like), organic bases (such as pyridine, triethylamine, tripropylamine, tributylamine, N,N-diisopropylethylamine, N-methylmorpholine, N,N-dimethylaminopyridine), and mixtures of any of the above. In a particular embodiment, the term "acid scavenger" refers to $KHCO_3$. In another particular embodiment, the term "acid scavenger" refers to N,N-diisopropylethylamine.

In the present context, the term "chemically pure" has its normal meaning within the art. Accordingly, an obtained compound which is at least 98% chemically pure comprises at most 2% chemical impurities. The chemical purity may be determined e.g. by HPLC. In the present context chemical purity is determined by % HPLC area.

DETAILED DESCRIPTION OF THE INVENTION

The inventors have found an improved process for producing naltrexone[17-(cyclopropylmethyl)-4,5α-epoxy-3,14-dihydroxy-morphinan-6-one] from noroxymorphone[4,5-α-epoxy-3,14-dihydroxy-morphinan-6-one] by alkylation with a cyclopropylmethyl halide in N-ethyl-2-pyrrolidone. The inventors have found that when running the alkylation in N-ethyl-2-pyrrolidone the reaction kinetics can be controlled efficiently and naltrexone is obtained as a chemically pure compound in a high yield.

In brief, noroxymorphone is mixed with cyclopropylmethyl halide in N-ethyl-2-pyrrolidone. In a preferred embodiment, the reaction is conducted in presence of an acid scavenger. The mixture is heated to a temperature in the range of 30 to 100° C., preferably in the range of 50-70° C., such as in the range of 50-60° C. Reaction time is adjusted in order to have a reasonably high conversion. Optionally, further cyclopropyl methyl halide is added to the mixture and optionally, the mixture is further heated to increase the conversion.

The formed naltrexone is isolated by a method comprising the following steps
 a) mixing the reaction mixture with an acid
 b) concentrating the reaction mixture
 c) mixing the resulting mixture with water
 d) optionally mixing the reaction mixture with an acid
 e) optionally treating the mixture with charcoal
 f) mixing the resulting mixture with a base
 g) isolating the resulting solid.
 h) optionally suspending the solid in water, mixing with acid followed by mixing with base and then isolating the resulting solid.
 i) drying the solid.

In one embodiment, prior to the reaction with cyclopropylmethyl halide; noroxymorphone is mixed with N-ethyl-2-pyrrolidone and a non-protic solvent whereupon the mixture of noroxymorphone, N-ethyl-2-pyrrolidinone and non-protic solvent is concentrated for example by distillation under vacuum.

The process of the present invention consistently gives pure naltrexone. The main impurity coming from alkylation of the hydroxyl group in the phenolic moiety is controlled with the process of the invention. The level of the impurity 3-cyclopropylmethylnaltrexone in the isolated naltrexone is below about 0.5% (by area) as measured by HPLC. The process of the invention also allows efficient removal of potentially unreacted noroxymorphone in isolated naltrexone.

Naltrexone prepared according to the method described in this invention can thus be directly used in the preparation of nalmefene e.g. by Wittig reaction. It is also envisaged in the present invention that such obtained nalmefene can be transformed into a suitable pharmaceutically acceptable salt form such as the hydrochloride salt. In a particular embodiment nalmefene hydrochloride is obtained as dihydrate form.

The present invention also relates to a pharmaceutical composition comprising nalmefene obtained from naltrexone obtained by the process of the invention. The pharmaceutical composition may further comprise at least one pharmaceutically acceptable excipient, carrier and/or diluent, and may be in a solid dosage form, such as a tablet, for oral administration.

Methods for the preparation of solid pharmaceutical preparations are well known in the art. See, e.g., Remington: The Science and Practice of Pharmacy, 21st ed., Lippincott Williams & Wilkins (2005). Solid preparations, such as tablets, may be prepared by mixing the active ingredients with an ordinary carrier, such as an adjuvant and/or diluent, and subsequently compressing the mixture in a tabletting machine. Non-limiting examples of adjuvants and/or diluents include: corn starch, lactose, talcum, magnesium stearate, gelatine, lactose, gums, and the like. Any other appropriate adjuvant or additive such as colourings, aroma, and preservatives may also be used provided that they are compatible with the active ingredients. The pharmaceutical compositions of the invention thus typically comprise an effective amount of nalmefene hydrochloride and one or more pharmaceutically acceptable carriers.

Nalmefene hydrochloride obtained according to the present invention may be administered in any suitable way, e.g. orally or parenterally, and it may be presented in any suitable form for such administration, e.g. in the form of tablets, capsules, powders, syrups or solutions or dispersions for injection. In one embodiment, the pharmaceutical composition will comprise nalmefene in a therapeutically effective amount. The term "therapeutically effective amount" refers to the amount/dose of a compound or pharmaceutical composition that is sufficient to produce an effective response (i.e., a biological or medical response of a tissue, system, animal or human sought by a researcher, veterinarian, medical doctor or other clinician) upon administration to a patient. The "therapeutically effective amount" will vary depending on, inter alia, the disease and its severity, and on the age, weight, physical condition and responsiveness of the patient to be treated. Furthermore, the "therapeutically effective amount" may vary if the compound of the invention is combined with one or more compounds: In such a case the amount of a given compound might be lower, such as a sub-effective amount.

Preferably, the amount of nalmefene hydrochloride in a pharmaceutical composition in unit dosage form is amount from about 10 mg to about 100 mg, such as from about 10 mg to about 60 mg, e.g. from about 10 mg to about 40 mg, or about 20 mg.

In one embodiment, nalmefene hydrochloride obtained according to the present invention constitutes an active ingredient in tablets, wherein said tablets further comprises lactose anhydrous, crospovidone, microcrystalline cellulose, magnesium stearate and Opadry OY-S-28849.

In an exemplary embodiment, nalmefene hydrochloride obtained according to the present invention constitutes an active ingredient in tablets with the composition of Table 1.

TABLE 1 nalmefene tablet composition, exemplary embodiment

| Content | Quantity |
| --- | --- |
| Nalmefene HCl dihydrate | 21.9 mg (~20 mg Nalmefene HCl) |
| Lactose Anhydrous | 60.7 mg |
| Crospovidone | 4.5 mg |
| Microcrystalline Cellulose | 61.4 mg |
| Magnesium Stearate | 1.5 mg |
| Total Core | 150 mg |
| Opadry OY-S-28849 White, consisting of: Hypromellose (5 mPa · S) Macrogol 400 Titanium dioxide (E171) Water, purified | 4.5 mg q.s. |
| Total film coated | 154.5 mg |
| Magnesium stearate | q.s. |

In particular, it is envisaged that a pharmaceutical composition of the present invention may be used for reduction of alcohol consumption in patients with alcohol dependence. In one embodiment, a composition comprising nalmefene HCl obtained by the present method may be used for the manufacture of a medicament for reduction of alcohol consumption in patients with alcohol dependence.

In another embodiment, the invention relates to a method for treating alcohol dependency, comprising administering a therapeutically effective amount of nalmefene HCl obtained by the present method, or a pharmaceutical composition thereof, to a patient in the need thereof.

The term "alcohol dependency" is a commonly known term for a skilled person. In the revised 4th edition of the Diagnostic and Statistical Manual of Mental Disorders (DSM-IVTR) (*Diagnostic and Statistical Manual of Mental Disorders*, 4th edition text revision, American Psychiatric Publishing, 2000), the term "alcohol dependency" is defined as the presence of three or more of the seven areas of life impairment related to alcohol in the same 12-month period. These impairments include tolerance, evidence of a withdrawal syndrome when alcohol is discontinued or intake is decreased, potential interference with life functioning associated with spending a great deal of time using alcohol, and returning to use despite evidence of physical or psychological problems.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

Embodiments According to the Invention

In the following, embodiments of the invention are disclosed. The first embodiment is denoted E1, the second embodiment is denoted E2 and so forth.

E1. A process for the manufacturing of naltrexone, comprising reacting noroxymorphone with cyclopropylmethyl halide in the presence of N-ethyl-2-pyrrolidone.

E2. The process according to embodiment 1, wherein the reaction takes place in the presence of an acid scavenger.

E3. The process according to embodiment 2, wherein the acid scavenger is an inorganic or organic base or a mixture thereof.

E4. The process according to any of embodiments 2-3, wherein the acid scavenger is N,N-diisopropylethylamine.

E5. The process according to any of embodiments 2-3, wherein the acid scavenger is potassium bicarbonate.

E6. The process according to any of embodiments 1-5, wherein the cyclopropylmethyl halide is cyclopropylmethyl bromide.

E7. The process according to any of embodiments 1-6, wherein the reaction takes place in the presence of a non-protic solvent.

E8. The process according to any of embodiments 1-7, wherein; prior to the reaction with cyclopropylmethyl halide; noroxymorphone is mixed with N-ethyl-2-pyrrolidone and a non-protic solvent whereupon the mixture of noroxymorphone, N-ethyl-2-pyrrolidinone and non-protic solvent is concentrated.

E9. The process according to embodiment 8, wherein said mixture of noroxymorphone, N-ethyl-2-pyrrolidinone and non-protic solvent is concentrated by distillation under vacuum.

E10. The process according to any of embodiments 7-9, wherein the non-protic solvent is toluene.

E11. The process according to any of embodiments 1-10, wherein N-ethyl-2-pyrrolidone is used in a weight by weight ratio of 0.5:1 to 10:1 in respect to noroxymorphone.

E12. The process according to embodiment 11, wherein N-ethyl-2-pyrrolidone is used in a weight by weight ratio of 1:1 to 5:1 with respect to noroxymorphone.

E13. The process according to embodiment 12, wherein N-ethyl-2-pyrrolidone is used in a weight by weight ratio of about 3:1 with respect to noroxymorphone.

E14. The process according to any of embodiments 1-13, wherein the molar relationship between noroxymorphone and acid scavenger is from about 1:0.5 to about 1:2.

E15. The process according to embodiment 14, wherein the molar relationship between noroxymorphone and acid scavenger is from about 1:1 to about 1:2.

E16. The process according to embodiment 15, wherein the molar relationship between noroxymorphone and acid scavenger is from about 1:1 to about 1:1.5.

E17. The process according to any of embodiments 1-16, wherein the molar relationship between noroxymorphone and cyclopropylmethyl halide is from about 1:1 to about 1:2.

E18. The process according to embodiment 17, wherein the molar relationship between noroxymorphone and cyclopropylmethyl halide is from about 1:1 to about 1:1.5.

E19. The process according to any of embodiments 1-18, wherein the reaction temperature is in the range of about 30-100° C.

E20. The process according to embodiment 19, wherein the reaction temperature is in the range of about 50-70° C., such as in the range of 50-55° C. or 55-60° C. or 60-65° C. or 65-70° C.

E21. The process according to any of embodiments 19-20, wherein the reaction temperature is in the range of about 50-60° C.

E22. The process according to any of embodiments 1-21, wherein the reaction is running for at least 8 hours; such as in the range of 8-48 hours, such as 8-12 hours, 12-16 hours, 16-20 hours, 20-24 hours, 24-28 hours, 28-32 hours, 32-36 hours, 36-40 hours, 40-44 hours or 44-48 hours.

E23. The process according to embodiment 22, wherein the reaction is running for a range of about 12-24 hours.

E24. The process according to embodiment 23, wherein the reaction is running for a range of about 16-20 hours.

E25. The process according to any of embodiments 1-24, wherein the formed naltrexone is isolated by a method comprising the following steps
a) mixing the reaction mixture with an acid
b) concentrating the reaction mixture
c) mixing the resulting mixture with water
d) optionally mixing the reaction mixture with an acid
e) optionally treating the mixture with charcoal
f) mixing the resulting mixture with a base
g) isolating the resulting solid.
h) optionally suspending the solid in water, mixing with acid followed by mixing with base and then isolating the resulting solid.
i) drying the solid.

E26. The process according to embodiment 25 wherein the acid in steps a), d) and h) is hydrochloric acid.

E27. The process according to any of embodiments 25-26, wherein the base in steps f) and h) is ammonium hydroxide.

E28. The process according to any of embodiments 1-27, wherein the formation of 3-cyclopropylmethyl-naltrexone is less than about 0.5% (by area).

E29. The process according to any of embodiments 1-28, wherein noroxymorphone is used as starting material in form of its free base or its hydrochloride salt.

E30. The process according to any of embodiments 1-29, wherein naltrexone is obtained as the free base.

E31. The process according to embodiment 30, wherein naltrexone free base is obtained as a hydrate.

E32. The process according to embodiment 31, wherein the naltrexone free base hydrate is a monohydrate.

E33. The process according to embodiment 32, wherein the naltrexone free base monohydrate is obtained in crystalline form.

E34. The process according to any of embodiments 1-33, wherein the naltrexone obtained from the process is further processed to give nalmefene.

E35. The process according to embodiment 34, wherein naltrexone obtained from the process is further processed by the Wittig reaction to give nalmefene.

E36. A process for the manufacturing of nalmefene comprising the steps
i) manufacturing of naltrexone by a process according to any of embodiments 1-33
ii) further processing of naltrexone obtained from i) to nalmefene optionally by the Wittig reaction.

E37. The process according to embodiment 36 comprising the following subsequent steps
iii) precipitating nalmefene as a pharmaceutically acceptable salt
iv) optionally purifying the obtained nalmefene salt.

E38. The process according to any of embodiments 34-37, wherein nalmefene is obtained as the hydrochloride.

E39. The process according to embodiment 38, wherein nalmefene hydrochloride is obtained as the dihydrate.

E40. The process according to embodiment 39, wherein nalmefene hydrochloride dihydrate is obtained in crystalline form.

E41. A process for manufacturing of a pharmaceutical composition, wherein the pharmaceutical composition comprises nalmefene obtained from the process according to any of embodiments 34-40.

E42. Naltrexone directly obtained from the process according to any of embodiments 1-33.

E43. Nalmefene directly obtained from the process according to any of embodiments 34-40.

E44. A pharmaceutical composition comprising nalmefene obtained from the process according to any of embodiments 34-40.

EXAMPLES

The invention will be illustrated by the following non-limiting examples.

| HPLC Chromatographic conditions | |
|---|---|
| Column: | Zorbax Eclipse XDB, 150 × 4.6 mm, 5 µm or equivalent |
| Mobile Phase A: | Buffer |
| Mobile Phase B: | Acetonitrile |
| Buffer: | 1.1 g of Sodium Octanesulfonate dissolved in 1 L of water, pH adjusted to 2.3 with $H_3PO_4$. |
| Column Temperature: | 35° C. |
| Detector: | UV at 230 nm |
| Flow: | 1.2 ml/min |
| Injection volume: | 20 µl |
| Time of Analysis: | 45 minutes |

TABLE 2

HPLC gradient

| Time | Mobile Phase A | Mobile Phase B |
|---|---|---|
| 0 | 90 | 10 |
| 45 | 55 | 45 |

Example 1

A mixture of noroxymorphone (52.7 g), N-ethyl-2-pyrrolidone (100 ml) and toluene (100 ml) was concentrated under vacuum at 80° C. The mixture was diluted with toluene (100 ml) and concentrated again. The suspension was diluted with N-ethyl-2-pyrrolidone (50 ml). Potassium bicarbonate (24.4 g) and cyclopropylmethyl bromide (29.3 g) were added and the mixture was heated up to 55° C. for 23 hours. The composition of the reaction mixture was checked by HPLC (% by area): naltrexone 97.3%, noroxymorphone 1.4%, 3-cyclopropylmethylnaltrexone 0.4%.

Example 2

Noroxymorphone (51.5 g) in N-ethyl-2-pyrrolidone (168 ml) and toluene (100 ml) was concentrated under vacuum at 80-85° C. Toluene was added (200 ml) and vacuum distillation repeated. Potassium bicarbonate (24.4 g) and cyclopropylmethyl bromide (29.3 g) were added and the mixture was heated up to 60° C. and maintained at that temperature for 22 hours. Further cyclopropylmethyl bromide (2.3 g) was charged and stirred at 60° C. for five additional hours. The composition of the reaction mixture was checked by HPLC: noroxymorphone 1.5%, naltrexone 97.4% and 3-cyclopropylmethyl naltrexone 0.3%. The reaction mixture was treated with HCl 10% (88.9 g) and concentrated under vacuum. The mixture was cooled and diluted with water (1580 g). Ammonium hydroxide 4% in water was added over 3 hours obtaining a suspension (pH 9.3). The suspension was stirred and then filtered. The solid was washed with water and dried under vacuum at 60° C. obtaining 55.9 g of naltexone. HPLC analysis (% by area): naltrexone 99.0%, noroxymorphone 0.1%, 3-cyclopropylmethyl naltrexone 0.3%.

Example 3

A mixture of noroxymorphone (52.7 g), potassium bicarbonate (24.4 g) and cyclopropylmethyl bromide (30.5 g) in N-ethyl-2-pyrrolidone (150 ml) was heated up 60° C. for 17 hours. The composition of the reaction mixture was checked by HPLC (% by area): naltrexone 95.7%, noroxymorphone 2.9%, 3-cyploroylmethylnaltrexone 0.3%.

Example 4

Noroxymorphone (52.7 g) in N-ethyl-2-pyrrolidone (100 ml) and toluene (100 ml) was concentrated under vacuum. Toluene was added (100 ml) and vacuum distillation repeated two more times. The mixture was diluted with N-ethyl-2-pyrrolidone. Cyclopropylmethyl bromide (30.5 g) and N,N-diisopropylethylamine (29.2 g) were added and the mixture was heated up to 60° C. and maintained at that temperature for 17 hours. The composition of the reaction mixture was checked by HPLC (% by area): naltrexone 95.0%, noroxymorphone 3.3%, 3-cyclopropylmethyl naltrexone 0.3%.

Example 5

A mixture of noroxymorphone (60 Kg, 0.209 Kmol), N-ethyl-2-pyrrolidinone (180 kg), cyclopropymethyl bromide (36.6 kg) and N,N-diisopropylethylamine (35.1 kg) was heated to 52-57° C. for 20 hours and 10 minutes. The mixture was then diluted with a solution prepared by mixing hydrochloric acid 37% (29 kg) and water (79 kg). Low boiling compounds were removed by distillation under vacuum keeping the temperature below 70° C. After cooling to 25-30° C. the mixture was further diluted with water (1910 kg). Ammonium hydroxide 4% (199 kg) was then added over three hours till pH=9-10 to precipitate the product. The solid was filtered, washed with water (2×120 kg) and dried under vacuum at 60° C. obtaining 68.5 kg of naltrexone (molar yield 93.2%). HPLC analysis (% by area): naltrexone 99.1%, noroxymorphone 0.11%, 3-cyclopropylmethylnaltrexone 0.41%

Example 6

A mixture of noroxymorphone (60 Kg, 0.209 Kmol), N-ethyl-2-pyrrolidinone (180 kg), cyclopropymethyl bromide (36.6 kg) and N,N-diisopropylethylamine (35.1 kg) was heated to 52-57° C. for 18 hours and 30 min. The mixture was then diluted with a solution prepared by mixing hydrochloric acid 37% (29 kg) and water (79 kg). Low boiling compounds were removed by distillation under vacuum keeping the temperature below 70° C. After cooling to 25-30° C. the mixture was further diluted with water (1910 kg). Ammonium hydroxide 4% (199 kg) was then added over three hours till pH=9-10 to precipitate the product. The solid was filtered, washed with water (2×120 kg) and dried under vacuum at 60° C. obtaining 69 kg of naltrexone (molar yield 89.7%). HPLC analysis (% by area): naltrexone 99.1%, noroxymorphone 0.09%, 3-cyclopropylmethylnaltrexone 0.41%

Example 7

A mixture of noroxymorphone (62 Kg), N-ethyl-2-pyrrolidinone (186 kg), cyclopropymethyl bromide (37.8 kg) and N,N-diisopropylethylamine (36.2 kg) was heated to 52-57° C. for 24 hours and 45 min. The mixture was then diluted with a solution prepared by mixing hydrochloric acid 37% (30 kg) and water (82 kg). Low boiling compounds were removed by distillation under vacuum keeping the temperature below 70° C. After cooling to 25-30° C. the mixture was further diluted with water (1975 kg). Ammonium hydroxide 4% (206 kg) was then added over three hours till pH=9-10 to precipitate the product. The solid was filtered, washed with water (2×124 kg) and dried under vacuum at 60° C. obtaining 71.3 kg of naltrexone (molar yield 89.6%). HPLC analysis (% by area): naltrexone 99.45%, noroxymorphone 0.16%, 3-cyclopropylmethylnaltrexone 0.28%

The invention claimed is:

1. A process for the manufacturing of naltrexone, comprising reacting noroxymorphone with cyclopropylmethyl halide in the presence of N-ethyl-2-pyrrolidone.

2. The process according to claim 1, wherein the reaction takes place in the presence of an acid scavenger.

3. The process according to claim 2, wherein the acid scavenger is an inorganic or organic base or a mixture thereof.

4. The process according to claim 1, wherein the cyclopropylmethyl halide is cyclopropylmethyl bromide.

5. The process according to claim 1, wherein; prior to the reaction with cyclopropylmethyl halide; noroxymorphone is mixed with N-ethyl-2-pyrrolidone and a non-protic solvent whereupon the mixture of noroxymorphone, N-ethyl-2-pyrrolidinone and non-protic solvent is concentrated.

6. The process according to claim 1, wherein N-ethyl-2-pyrrolidone is used in a weight by weight ratio of 0.5:1 to 10:1 with respect to noroxymorphone.

7. The process according to claim 2, wherein the molar relationship between noroxymorphone and acid scavenger is from about 1:0.5 to about 1:2.

8. The process according to claim 1, wherein the molar relationship between noroxymorphone and cyclopropylmethyl halide is from about 1:1 to about 1:2.

9. The process according to claim 1, wherein the reaction temperature is in the range of about 30-100° C.

10. The process according to claim 9, wherein the reaction temperature is in the range of about 50-70° C.

11. The process according to claim 1, wherein the formed naltrexone is isolated by a method comprising the following steps
   a) mixing the reaction mixture with an acid
   b) concentrating the reaction mixture
   c) mixing the resulting mixture with water
   d) optionally mixing the reaction mixture with an acid
   e) optionally treating the mixture with charcoal
   f) mixing the resulting mixture with a base
   g) isolating the resulting solid
   h) optionally suspending the solid in water, mixing with acid followed by mixing with base and then isolating the resulting solid
   i) drying the solid.

12. The process according to claim 11 further comprising further processing of naltrexone obtained from step i) to nalmefene optionally by the Wittig reaction.

13. The process according to claim 12 comprising the following subsequent steps
   iii) precipitating nalmefene as a pharmaceutically acceptable salt
   iv) optionally purifying the obtained nalmefene salt.

* * * * *